United States Patent [19]
Kato et al.

[11] 3,931,146
[45] Jan. 6, 1976

[54] HYDROGENATED PULLULAN

[75] Inventors: Koso Kato; Makoto Shiosaka, both of Okayama, Japan

[73] Assignee: Hayashibara Biochemical Laboratories, Incorporated, Japan

[22] Filed: May 28, 1974

[21] Appl. No.: 473,749

[30] Foreign Application Priority Data
June 1, 1973   Japan.............................. 48-62277

[52] U.S. Cl................................. 260/209; 264/165
[51] Int. Cl.² .......................................... C07G 3/00
[58] Field of Search ................................. 260/209 R

[56] References Cited
UNITED STATES PATENTS
3,277,077   10/1966   Holly et al. ..................... 260/209 R Primary Examiner—Johnnie R. Brown
Assistant Examiner—Cary Owens
Attorney, Agent, or Firm—Hans Berman; Kurt Kelman

[57] ABSTRACT

Hydrogenated pullulan is produced by the reaction of an aqueous solution of pullulan with hydrogen gas under pressure in the presence of suitable catalysts until the reducing property of the solution disappears. The hydrogenated pullulan is much more resistant to heat than pullulan and its aqueous solution hardly loses viscosity and is not colored under heat treatment. The hydrogenated pullulan is much less absorbable by the intestinal walls than pullulan so as to reduce more effectively the caloric value of foods when it is mixed with foods. Shaped bodies such as films, sheets, plates, capsules, containers, coatings and fibers are readily prepared in a conventional manner. The films are practically impervious to atmospheric oxygen and suitable as packaging material.

1 Claim, No Drawings

HYDROGENATED PULLULAN

The present invention relates to hydrogenated pullulan.

Pullulan is a neutral, viscous polysaccharide consisting of maltotriose units linked by $\alpha$-1,6-glucosidic bonds. Pullulan is readily prepared by inoculating a strain of Aureobasidium in a culture medium containing at least one saccharide such as glucose, sucrose, fructose, dextrose, dates extracts, partial hydrolyzates of starch and culturing in said medium under aerobic conditions. The culture broth is filtered to remove the cells and pullulan is precipitated by addition of organic solvents, such as methanol and ethanol to the filtrate. Pullulan having different molecular weight can be obtained by varying the composition of the culture medium or culture conditions.

Among the strains belonging to the genus Aureobasidium, for example, *Aureobasidium pullulans*, IFO 4464, IFO 4875, IFO 6353, IFO 6401, IFO 6402, IFO 6725 can be employed.

Pullulan has been utilized widely in shaped bodies which do not cause environmental pollution upon disposal and for the protection of substances sensitive to oxygen, such as foods and pharmaceuticals. Furthermore pullulan is used in low coloric foods and beverages since it is neither digested in the intestinal tract nor obsorbed therefrom.

The viscosity of the aqueous solution of pullulan decreases markedly at temperatures above 100°C. The aqueous solutions of other polysaccharides such as starch and cellulose do not show such decrease of viscosity. This property of pullulan has caused trouble in the processing of pullulan.

The decrease of viscosity of pullulan at high temperature is due to the decomposition of pullulan into smaller molecules.

Heat also causes the discoloration of pullulan which reduces the commercial value of products made from pullulan.

It has now been found that hydrogenated pullulan is much more resistant to heat than pullulan and such thermostability can not be anticipated from the properties and the chemical structure of pullulan. Comparison of the characteristics of hydrogenated pullulan with those of pullulan reveals that the water solubility of hydrogenated pullulan and the oxygen permeability of the films prepared therefrom are almost the same as those of pullulan, but that hydrogenated pullulan is less biodegradable by enzymes than pullulan.

The average molecular weight of the hydrogenated pullulan of the present invention is between 10,000 and 5,000,000.

Pullulan is not decomposed and the hydrogenation of pullulan is carried out effectively, when catalysts, for example Raney nickel are added to a 1 to 40% aqueous solution of pullulan in an amount of 0.1 to 15% by weight of pullulan and the hydrogenation is carried out at a preferred reaction temperature of 40°C to 150°C under a hydrogen pressure of 20 kg/cm$^2$ to 150 kg/cm$^2$.

The pH of the reaction mixture should be 5 to 10 to prevent decomposition of the pullulan. As the pH of the reaction mixture is apt to decrease in the course of reaction, neutralizing agents, if desired, are added to the mixture in an amount not to inhibit the catalytic action. It is preferred to add neutralizing agents such as caustic alkali, calcium carbonate and magnesium carbonate to the mixture in an amount of 0.01 to 1.0% based on the weight of pullulan.

Insoluble materials such as catalysts and neutralizing agents are filtered off from the hydrogenation mixture.

The filtrate is decolorized with active carbon, deionized with ion-exchange resins and then concentrated under reduced pressure to yield a 5 to 40% solution of hydrogenated pullulan.

Hydrogenated pullulan having a moisture content of less than 10% was obtained as a white powder by spray-drying the solution at a pressure of 100 to 300 kg/cm$^2$ at 90° to 160°C. The reducing power of the hydrogenated pullulan thus obtained was determined in accordance with the Somogyi-Nelson method, but none was detected. The hydrogenated pullulan can be used like pullulan but also employed as the material for various shaped bodies which must resist high temperature and have no permeability to oxygen, for example, films, capsules, fibers, sheets etc. It is also used for low caloric foods and beverages without heat decomposition.

When the hydrogenated pullulan is used as a main ingredient of low caloric foods, for example, baked products, cookies, biscuits, it can be mixed with flour or amylose to obtain a product with excellent properties. It can also be mixed with non-caloric sweetner, maltitol or eggs for preparing non-caloric foods.

Experiments comparing pullulan with hydrogenated pullulan are described below.

EXPERIMENT 1.

Viscosity loss by heat treatment.

The pullulan and the hydrogenated pullulan employed in the experiment were obtained according to the method described in Example 1a, b and Example 2a, b respectively.

A 10% aqueous solution of each material was maintained at pH 6.0 and 140°C for 60 minutes. Viscosity was tested with an Ostwald-Viscometer at 40°C. The loss of viscosity calculated from Viscosity after heat treatment - Viscosity before heat treatment Viscosity before heat treatment is given in Table 1.

Table 1

| Molecular weight | Pullulan | Hydrogenated pullulan |
|---|---|---|
| 400,000 | 25% | 3% |
| 50,000 | 10% | 2% |

As is evident from these results, the thermal loss of viscosity of hydrogenated pullulan is 1/5 – 1/8 of that of pullulan.

EXPERIMENT 2.

Discoloration by heat treatment.

The samples employed and the heat treatment were the same as in Experiment 1. The color value is indicated by the difference of the absorbance at 750 nm from that at 420 nm. The absorbance was measured in the 5 cm cell of a spectrophotometer (Hitachi Ltd. Model 124).

Values shown in Table 2 were obtained by subtraction of the color value before heat treatment from that after heat treatment.

Table 2

| Molecular weight | Pullulan | Hydrogenated pullulan |
|---|---|---|
| 400,000 | 0.130 | 0.020 |
| 50,000 | 0.165 | 0.020 |

These results indicate that hydrogenated pullulan is hardly discolored by heat treatment.

EXPERIMENT 3.

Enzymatic decomposition.

The samples of pullulan and hydrogenated pullulan were the same as in Experiments 1 and 2. One ml aliquots of an enzyme extracted from the mucosa of the small intestine in a pig, of acetone precipitated powder of an enzyme extracted from pig liver and of an enzyme extracted from pig pancreas which are similar to human digestive enzymes, and human saliva enzyme amylase respectively were mixed with 7 ml of a buffer solution and 2 ml of 1% solution the pullulan and of hydrogenated pullulan. The mixtures were incubated at 37°C. Aliquots were collected at certain intervals and the reducing sugars formed were determined in accordance with the Somogyi-Nelson method after removing proteins. The amounts of the formed reducing sugars from 20 mg of samples are listed in mg of glucose in Table 3.

Table 3

| Enzyme | Reaction pH | Pullulan 3 | Pullulan 22 | Hydrogenated pullulan 3 | Hydrogenated pullulan 22 |
|---|---|---|---|---|---|
| Pig intestine | 6.8 | trace | 0.68 | 0 | 0.30 |
| Pig pancreas | 5.0 | 0.49 | 0.91 | 0.23 | 0.42 |
| Human saliva α-amylase | 6.0 | 0.48 | 2.23 | 0.21 | 0.98 |
| Pig liver | 6.8 | 0.69 | 1.80 | 0.25 | 0.79 |

As the above results show, hydrogenated pullulan is more difficult to decompose by enzymes than pullulan. After oral administration of an aqueous 3% solution of hydrogenated pullulan to rabbits having fasted for 24 hours, the blood sugar level did not increase significantly. Both ends of the small intestines of fasting rabbits were ligated and 5% aqueous solution of pullulan and hydrogenated pullulan was injected into said small intestines respectively. After three hours the intestines were washed and the total sugars in the washings were determined. Recovery of the injected pullulan and hydrogenated pullulan was 95 and 98% respectively. Consequently, the hydrogenated pullulan is less absorbed than pullulan.

The following examples further illustrate the present invention.

EXAMPLE 1.

Preparation of pullulan.

a. As a seed culture, Aureobasidium pullulans IFO 4464 was inoculated in a culture medium consisting of 10% starch partial hydrolyzate (D.E. 50), 0.2% $K_2HPO_4$, 0.2% NaCl, 0.2% Peptone, 0.04% $MgSO_4 \cdot 7H_2O$, 0.001% $FeSO_4 \cdot 7H_2O$, and tap water at an initial pH of 7.0 and cultured with shaking at 27°C for 2 days under aerobic conditions. $2^{v/v\%}$ of culture broth thus obtained was added to the main culture medium whose composition was the same as that of the seed culture medium, and cultured at 27°C for 7 days under aerobic conditions. The broth was filtered to remove the cells and to the filtrate thus obtained there was added an active carbon powder in an amount of 1% based on the weight of sugar.

After decoloration, an equal amount of methanol was added to the carbon-free filtrate.

The precipitate formed was recovered by centrifugation, washed with methanol and dried in vacuo. The average molecular weight of the pullulan thus obtained was 400,000 and the yield to the starting sugar was 60%.

b. Aureobasidium pullulans IFO 6353 was incubated for 7 days in the same culture medium as in Example 1. (a) except that the content of $K_2HPO_4$ was 0.5%. The subsequent purification was also carried out in accordance with the method in Example 1a. The average molecular weight of the pullulan thus obtained was 50,000 and the yield based on the starting sugars was 70%.

EXAMPLE 2.

Preparation of hydrogenated pullulan.

a. Raney nickel and calcium carbonate were added to 10% aqueous solution of the pullulan obtained in Example 1a in respective amounts of 10% and 0.2 of the pullulan, and the mixture was placed in an autoclave. The reaction temperature was raised from room temperature at 2°C per minute at a hydrogen gas pressure of 100 kg/cm². After the reaction temperature reached 120°C, the hydrogen gas pressure of 100 kg/cm² was maintained for 8 hours.

Insoluble materials such as catalyst, neutralizing agent etc. were removed by centrifugation. Active carbon was added to the supernatant thus obtained in an amount of 0.5% based on the weight of initial pullulan to decolorize the solution with stirring at 60°C for 1 hour. The decolorized solution was deionized with H type cation exchange resin and OH type anion exchange resin. The deionized solution thus obtained was concentrated under reduced pressure to 15% of its original volume and then dried by spraying from a nozzle at 130°C into hot air under a pressure of 250 kg/cm².

The white powder of hydrogenated pullulan thus obtained contained 2.5% moisture and the yield was 88% based on pullulan. The reducing power of this hydrogenated pullulan was tested in accordance with the Somogyi-Nelson method, and none was detected.

b. To a 15% aqueous solution of pullulan obtained in Example 1b and having a molecular weight of 50,000 calcium carbonate and Raney nickel in respective amounts of 0.1 and 8% respectively based on the weight of pullulan were added. Hydrogenation and purification were carried out as in Example 2a.

The hydrogenated pullulan solution thus obtained was concentrated to 30% and spray-dried at 130°C under a pressure of 200 kg/cm².

A white powder of hydrogenated pullulan having a moisture content of 2.0% was obtained in a yield of 93% against pullulan. The reducing power of the hydrogenated pullulan was tested in accordance with the Somogyi-Nelson method, and no reducing power was detected.

What is claimed is:

1. Hydrogenated pullulan produced by reacting an aqueous solution of pullulan with hydrogen gas under a pressure of 20 to 150 kg/cm² in the presence of a hydrogenation catalyst until said pullulan is free from reducing power capable of being detected by the method of Somogyi-Nelson.

* * * * *

UNITED STATES PATENT AND TRADEMARK OFFICE
CERTIFICATE OF CORRECTION

PATENT NO. : 3,931,146
DATED : January 6, 1976
INVENTOR(S) : KOSO KATO

It is certified that error appears in the above-identified patent and that said Letters Patent are hereby corrected as shown below:

In the heading, line [73], after "Incorporated", insert

-- Okayama-ken, --

Signed and Sealed this twenty-third Day of March 1976

[SEAL]

Attest:

RUTH C. MASON
*Attesting Officer*

C. MARSHALL DANN
*Commissioner of Patents and Trademarks*